(12) United States Patent
Huang et al.

(10) Patent No.: US 11,618,957 B2
(45) Date of Patent: Apr. 4, 2023

(54) ELECTROLYSIS DEVICE

(71) Applicant: Colgate-Palmolive Company, New York, NY (US)

(72) Inventors: Chun Huang, Somerset, NJ (US); Paloma Pimenta, Staten Island, NY (US); Guofeng Xu, Plainsboro, NJ (US); Matthew Lee Kolb, Upper Black Eddy, PA (US)

(73) Assignee: Colgate-Palmolive Company, New York, NY (US)

( * ) Notice: Subject to any disclaimer, the term of this patent is extended or adjusted under 35 U.S.C. 154(b) by 824 days.

(21) Appl. No.: 16/578,486

(22) Filed: Sep. 23, 2019

(65) Prior Publication Data

US 2020/0121434 A1   Apr. 23, 2020

Related U.S. Application Data

(60) Provisional application No. 62/747,287, filed on Oct. 18, 2018.

(51) Int. Cl.
 *C25B 15/023* (2021.01)
 *A61C 19/06* (2006.01)
 (Continued)

(52) U.S. Cl.
 CPC .......... *C25B 15/023* (2021.01); *A61C 19/066* (2013.01); *C01B 11/06* (2013.01); *C25B 9/17* (2021.01); *C25B 15/02* (2013.01)

(58) Field of Classification Search
 CPC ..... A61C 19/066; C25B 15/02; C25B 15/023; C25B 9/17; C25B 1/26; C02F 1/4674; C02F 1/46104
 See application file for complete search history.

(56) References Cited

U.S. PATENT DOCUMENTS 7,515,507 B2   4/2009 Nanda
8,156,602 B2   4/2012 Jimenez et al.
(Continued)

FOREIGN PATENT DOCUMENTS

CN   101909641   12/2010
CN   103458852   12/2013
(Continued)

OTHER PUBLICATIONS

WO 2016157570 A1 translation (Year: 2016).*
(Continued)

*Primary Examiner* — Nicholas A Smith

(57) ABSTRACT

An electrolysis device may include: a housing comprising a container having an open end, the container configured to contain a liquid when the container is oriented in an upright position; and an electrolysis circuit comprising: a power source; a plurality of electrodes disposed within the container and electrically coupled to the power source; an orientation switch electrically coupled to the power source, coupled to the housing, and oriented to switch when the container is oriented in the upright position; and a control circuit electrically coupled to the power source, the electrodes, and the orientation switch, wherein the electrolysis circuit is configured to operate when the electrodes pass an electric current above a predetermined current threshold and the container is oriented in the upright position.

18 Claims, 8 Drawing Sheets

(51) Int. Cl.
*C25B 15/02* (2021.01)
*C25B 9/17* (2021.01)
*C01B 11/06* (2006.01)

(56) References Cited

U.S. PATENT DOCUMENTS

| | | | |
|---|---|---|---|
| 9,999,581 | B2 | 6/2018 | Matin et al. |
| 10,179,038 | B2 | 1/2019 | Johansson |
| 2004/0213698 | A1 | 10/2004 | Mcgrew |
| 2010/0285150 | A1 | 11/2010 | Noguchi |
| 2017/0367943 | A1 | 12/2017 | Johansson |
| 2019/0110876 | A1 | 4/2019 | Johansson |
| 2019/0186025 | A1 | 6/2019 | Johansson |
| 2019/0360109 | A1* | 11/2019 | Jeon .................. C02F 1/46104 |

FOREIGN PATENT DOCUMENTS

| | | |
|---|---|---|
| CN | 106746056 | 5/2017 |
| CN | 206173056 | 5/2017 |
| CN | 206979277 | 2/2018 |
| CN | 108624904 | 10/2018 |
| JP | 4822763 | 11/2011 |
| JP | 2018-158285 | 10/2018 |
| WO | WO-2016157570 A1 * 10/2016 ................ C02F 1/46 |
| WO | 2018/015570 | 1/2018 |
| WO | 2018/048393 | 3/2018 |

OTHER PUBLICATIONS

CN-106746056-A translation (Year: 2017).*
International Search Report and Written Opinion of the International Searching Authority in International Application No. PCT/US2019/052327, dated Dec. 10, 2019.

* cited by examiner

ELECTROLYSIS DEVICE

CROSS-REFERENCE TO RELATED APPLICATIONS

The present application claims priority to U.S. Provisional Patent Application Ser. No. 62/747,287, filed on Oct. 18, 2018, the entirety of which is incorporated herein by reference.

BACKGROUND

Many teeth whitening products currently available on the market contain hydrogen peroxide, which serves as a bleaching agent for teeth. However, most mouthwash products are formulated at a low pH of between 4.5-5.5 in order to avoid shelf life stability issues that are associated with higher pH hydrogen peroxide formulas. The issue with the lower pH formulations is that they have reduced whitening efficacy because hydrogen peroxide is more stable and has lower oxidation potential at lower pH. Another issue for products that include hydrogen peroxide is the regulation of hydrogen peroxide in oral care products. For example, in Europe, the concentration of hydrogen peroxide has to be kept less than 0.1% for over the counter products. Regulations, therefore, can lead directly to reduced whitening efficacy for hydrogen peroxide products.

Hypochlorite is known to be an efficient bleaching agent. It has been widely used in industry and in the daily life by consumers as a bleach ingredient. Hence, a solution containing hypochlorite could be used as a mouthwash product to provide consumers with at home teeth whitening benefits while avoiding the regulatory and stability issues associated with hydrogen peroxide. However, hypochlorite can still have stability issues when stored at room temperature. It is therefore desirable to enable delivery of a hypochlorite solution to the consumer while also avoiding stability issues.

BRIEF SUMMARY

Exemplary embodiments according to the present disclosure are directed to an electrolysis device which converts a precursor solution into an oral care solution. The electrolysis device includes electrodes, a power source, and a control circuit so that the electrodes may be powered when submerged in the precursor solution, thereby delivering an oral care solution following electrolysis of the precursor solution. The electrolysis device may be incorporated as part of a system which is used to deliver the precursor solution to the consumer.

In one aspect, the invention can be an electrolysis device including: a housing comprising a container having an open end, the container configured to contain a liquid when the container is oriented in an upright position; and an electrolysis circuit comprising: a power source; a plurality of electrodes disposed within the container and electrically coupled to the power source; an orientation switch electrically coupled to the power source, coupled to the housing, and oriented to switch to a closed position when the container is oriented in the upright position; and a control circuit electrically coupled to the power source, the electrodes, and the orientation switch, wherein the electrolysis circuit is configured to operate when the electrodes pass an electric current above a predetermined current threshold and the container is oriented in the upright position.

In another aspect, the invention can be a system for delivering an oral care solution, the system including: an electrolysis device comprising: a housing comprising a first container having an open end, the first container configured to contain a liquid when the first container is oriented in an upright position; and an electrolysis circuit comprising: a power source; a plurality of electrodes disposed within the container and electrically coupled to the power source; an orientation switch electrically coupled to the power source, coupled to the housing, and oriented to switch to a closed position when the first container is oriented in the upright position; and a control circuit electrically coupled to the power source, the electrodes, and the orientation switch, wherein the electrolysis circuit is configured to operate when the electrodes pass an electric current above a predetermined current threshold and the first container is oriented in the upright position; and a second container configured to contain a precursor solution, wherein the housing of the electrolysis device comprises a first threaded coupling, and an opening of the second container comprises a second threaded coupling, the first threaded coupling configured to threadably engage the second threaded coupling such that the housing seals the second container.

In still another aspect, the invention can be a system for delivering an oral care solution, the system including: a bottle comprising a first container, a second container positioned above the first container, and a tube fluidically coupling the first container to the second container, wherein the second container includes an open end; a cap comprising an electrolysis circuit and a housing, the housing configured to couple to the second container at the open end, the electrolysis circuit comprising: a power source; a plurality of electrodes extending away from the housing and electrically coupled to the power source; a pressure switch electrically coupled to the power source and positioned to be switched to a closed position when the cap is coupled to the second container; and a control circuit electrically coupled to the power source, the electrodes, and the pressure switch, wherein the electrolysis circuit is configured to operate when the electrodes pass an electric current above a predetermined current threshold and the pressure switch is in the closed position.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The foregoing summary, as well as the following detailed description of the exemplary embodiments, will be better understood when read in conjunction with the appended drawings. It should be understood, however, that the invention is not limited to the precise arrangements and instrumentalities shown in the following figures.

DETAILED DESCRIPTION

Figure 1:
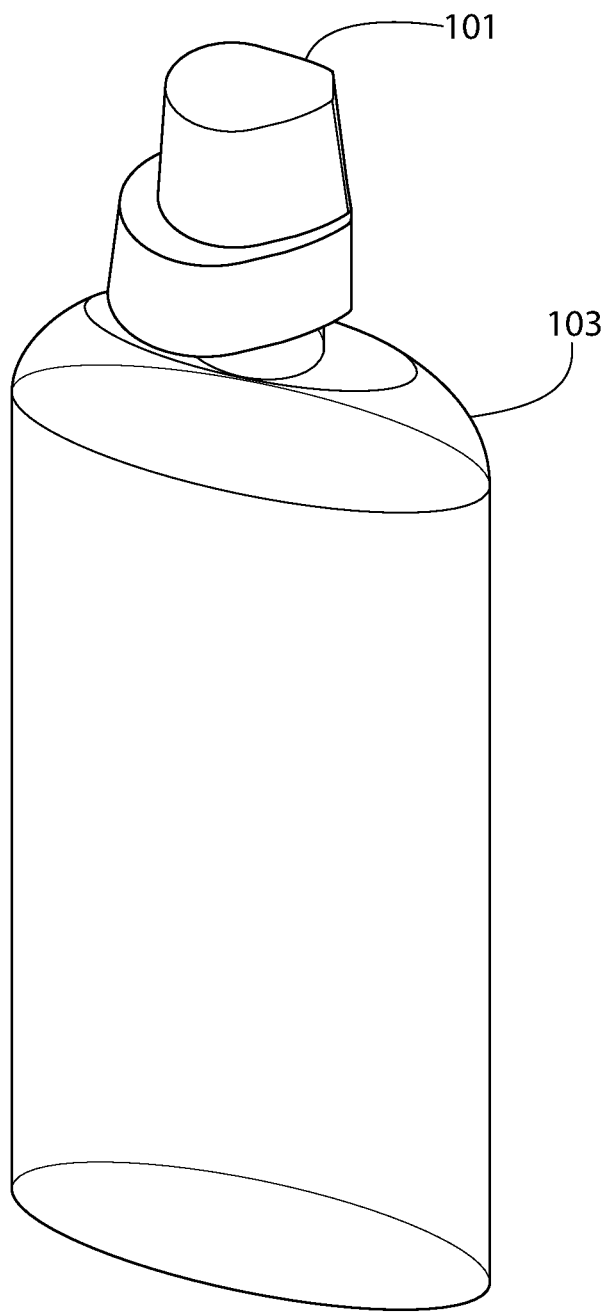
FIG. 1 illustrates an electrolysis device in accordance with a first embodiment of the present invention, the electrolysis device being coupled to a bottle.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention expressly should not be limited to such preferred embodiments illustrating some possible non-limiting combinations of features that may exist alone or in other combinations of features; the scope of the invention being defined by the claims appended hereto.

Figure 2:
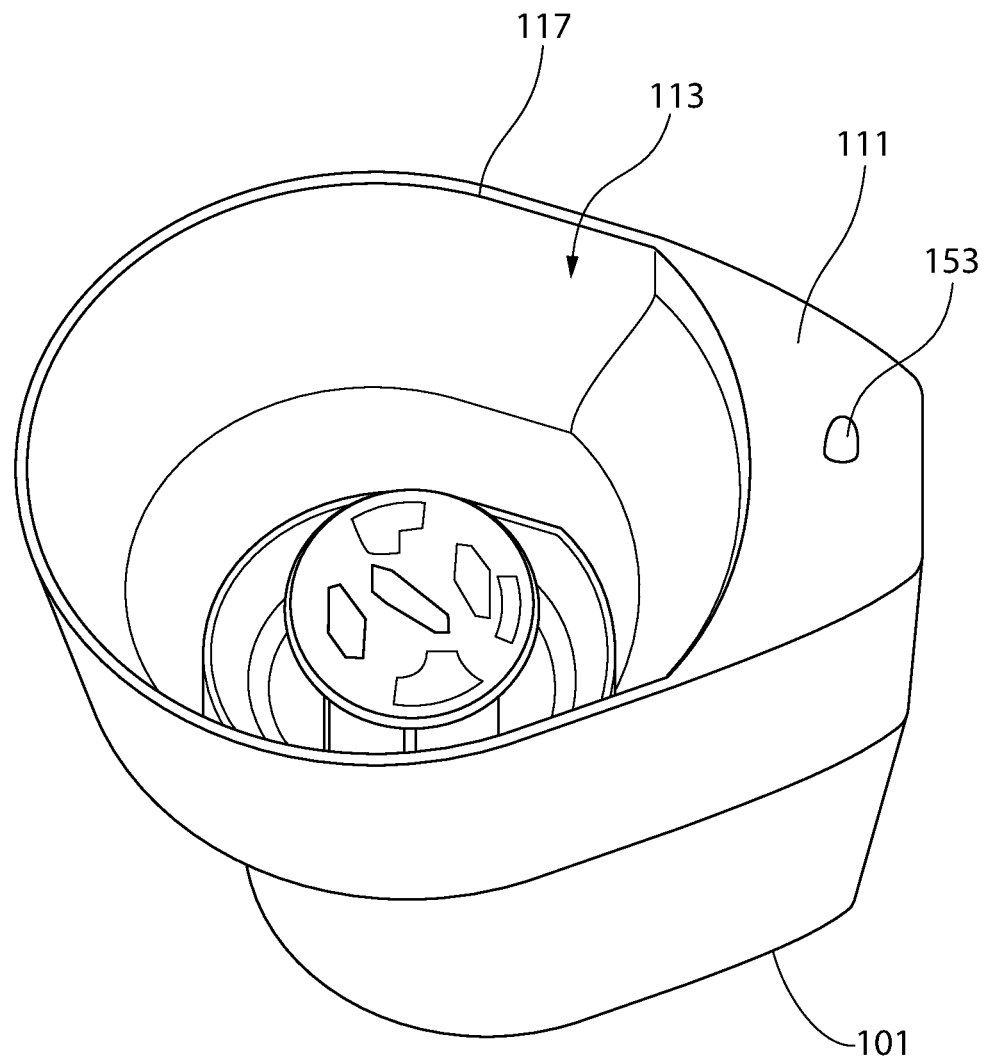
FIG. 2 illustrates a bottom perspective view of the electrolysis device of FIG. 1.

Turning to FIGS. 1-2, an electrolysis device 101 is illustrated in accordance with an embodiment of the present invention. The electrolysis device 101 is coupled to a bottle 103, which may contain a precursor solution. In certain embodiments, the electrolysis device 101 may be used without the presence or need of the bottle 103. In certain other embodiments, the electrolysis device 101 and the bottle 103 are both part of a system for delivering an oral care solution to a user. In certain embodiments, the oral care solution may be a hypochlorite solution. In certain embodiments, the electrolysis device 101 may serve as a cap to the bottle 103, and part of the electrolysis device 101 includes a container in which electrolysis may take place.

A hypochlorite solution may be generated in the container of the electrolysis device 101 by in-situ electrolysis of a precursor solution which includes sodium chloride. In certain embodiments, the precursor solution may be 3% NaCl in a phosphate buffer, which may be, for example, a solution of 2% $NaH_2PO_3.H_2O$ and 0.1% $Na_2HPO_3$. In certain embodiments, the precursor solution has a pH of about 6.0-7.0. And in still other embodiments, the precursor solution has a pH of about 6.5. Of course, the components of the precursor solution are not to be limiting of the invention unless expressly stated in the claims. In certain embodiments, after applying electrolysis to a precursor solution of 3% NaCl, the resulting hypochlorite solution will have a pH that is not significantly different from the pH of the precursor solution. Although other precursor solutions may be used to generate oral care solutions other than hypochlorite, for ease of description, the invention is described in terms of the oral care solution being a hypochlorite solution from this point forward.

Using this electrolysis device, an effective amount of hypochlorite can be generated in a relatively short time period, and this amount can be significant in providing a significant teeth whitening efficacy to the user, especially as compared to whitening mouthwashes and whitening toothpastes that currently exist on the market. Through this on-the-spot electrolysis approach, the whitening efficacy of the hypochlorite solution can benefit the user without the problems associated with ensuring stability of the hypochlorite solution during manufacture, packaging, distribution, and/or sitting on store shelves or in the homes of users.

Figure 3:
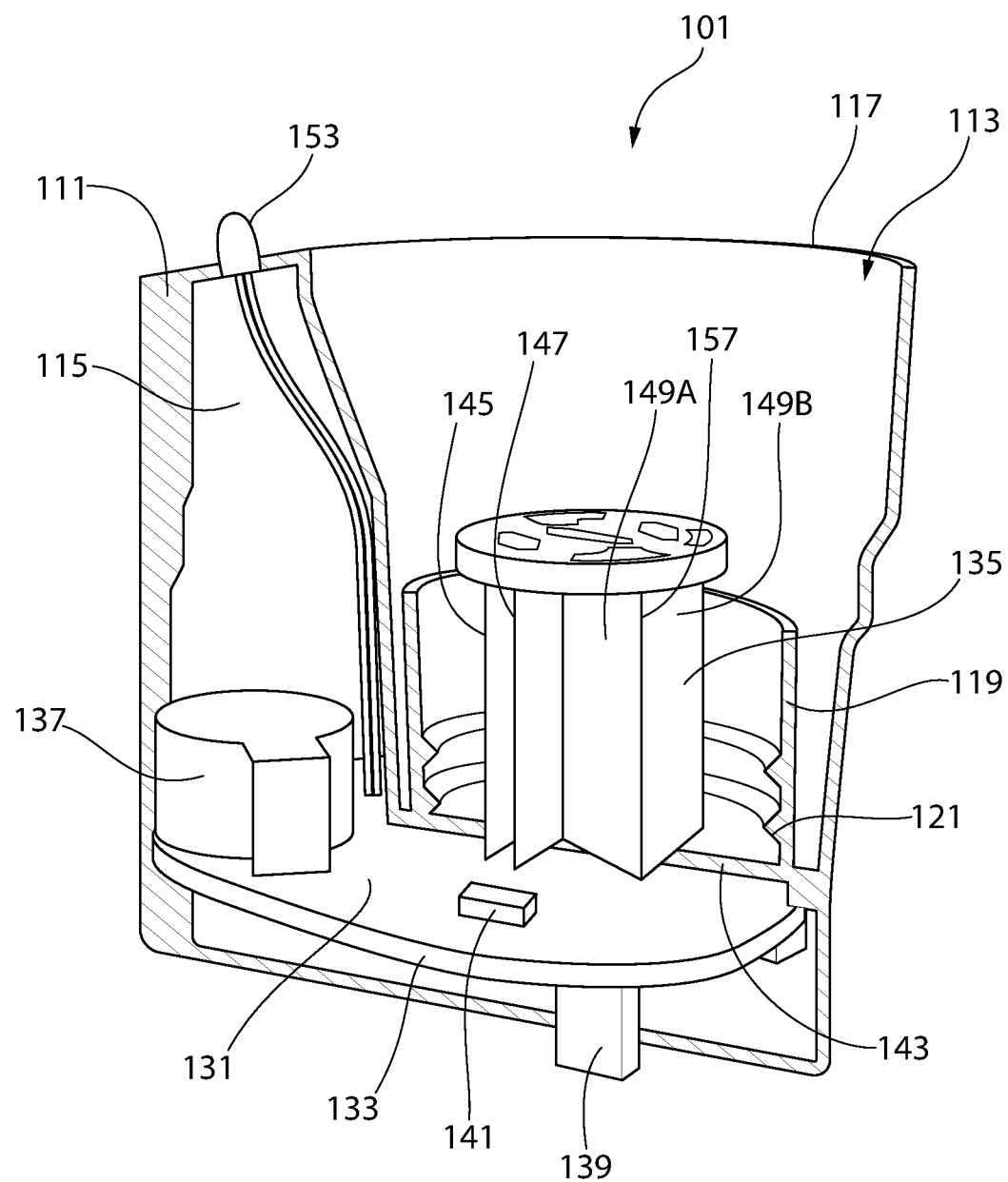
FIG. 3 illustrates a sectional view of the electrolysis device of FIG. 1.

Referring to FIGS. 2-3, the electrolysis device 101 includes a housing 111 which forms the container 113 and an enclosure 115. The container 113 includes an open end 117 so that the container 113 is formed as a cup. The housing 111 also includes a circular wall 119 within the container 113, and the circular wall 119 includes threads 121 extending inward therefrom. The circular wall 119 and threads 121 are arranged to engage the top of the bottle 103 which includes a set of complementary threads, so that the housing 111 of the electrolysis device 101 may be affixed to and seal the bottle. In certain embodiments, the circular wall 119 and threads 121 may be omitted, and in such embodiments, the housing 111 of the electrolysis device 101 would not be configured to sealingly engage the bottle 103.

The enclosure 115 in the embodiment shown is sealed to keep out moisture, and components of the electrolysis device 101 are located within the enclosure 115. In certain embodiments, the enclosure 115 may have an access door to provide a user with access to the components of the electrolysis device 101 located within the enclosure 115. In certain other embodiments, the enclosure 115 may have an open access window to provide a user with access to the components of the electrolysis device 101 located within the enclosure 115.

The electrolysis device 101 includes an electrolysis circuit 131 which is configured to initiate and control electrolysis of the precursor solution. The electrolysis circuit 131 includes a circuit board 133 located within the enclosure 115. The circuit board 133 facilitates electrical coupling of the other components, in that all other components of the electrolysis circuit 131 may be electrically coupled to the circuit board 133. In certain embodiments, the circuit board 133 may be excluded from the electrolysis circuit 131, and in such embodiments, the other components of the electrolysis circuit 131 may be directly coupled to each other as needed for proper functioning of the electrolysis circuit 131. In certain other embodiments, some of the components of the electrolysis circuit 131 may be electrically coupled to the circuit board 133, while other components are electrically coupled directly to each other. The electrolysis circuit 131 includes a plurality of electrodes 135 located within the container 113, surrounded by the circular wall 119. Other components of the electrolysis circuit 131 are also located within the enclosure 115, including: a power source 137, an orientation switch 139, and a control circuit 141. With the electrodes 135 located in the container 113 and the circuit board 133 located in the enclosure 115, it is necessary for an electrical connection between these two components to pass through the wall 143 separating the container 113 from the enclosure 115. Such electrical connections should be protected from the precursor solution by a protective silicone barrier or any other appropriate material that provides a barrier against moisture and is non-reactive with the precursor solution. In certain embodiments, it may be desirable for the wall 143 to be entirely covered within the container 113 with a silicone barrier to ensure that moisture does not permeate into the enclosure 115 and degrade the components of the electrolysis circuit 131 therein.

The plurality of electrodes 135 includes a first electrode 145 and a second electrode 147 secured between the wall 143 and an end plate 149, with each of the electrodes 135 being electrically coupled to the circuit board 133. The first and second electrodes 145, 147 are formed as parallel plate electrodes in the embodiment shown, with the spacing between the electrodes 145, 147 being substantially constant. In order to increase the volume of space between the electrodes 145, 147 within the limited space of the container 113, each of the electrodes 145, 147 includes non-parallel plate sections 149A, 149B that are adjoined at a fold 151. And, each of the electrodes 145, 147 may include more than two non-parallel plate sections 149A, 149B and more than one fold 151, with each fold 151 adjoining two of the plate sections for each electrode 145, 147. Each of the folds 151 in the first electrode 145 is parallel to one of the folds in the second electrode 147. The inclusion of multiple non-parallel plate sections in each of the electrodes 145, 147 makes it possible to increase the volume of space between the electrodes 145, 147 without actually increasing the spacing between the electrodes or requiring additional space within the container 113. With this configuration, the precursor solution can be more efficiently converted into the hypochlorite solution because of the increased volume between the electrodes 145, 147.

The power source 137 provides operating power to each of the other components of the electrolysis circuit 131, and in the embodiment shown, the power source 137 is a battery. In certain embodiments, the power source 137 may be a rechargeable battery. In still other embodiments, the power source 137 may be an external power source. In certain embodiments, the power source 137 provides up to 9 volts of power to the electrodes 135. In still other embodiments, the power source 137 may provide more or less voltage to the electrodes 135. However, when less voltage is provided to the electrodes 135, the time period needed for the electrolysis process to generate a solution with an effective amount of hypochlorite is increased. Similarly, when a greater voltage is provided to the electrodes 135, the time period needed for the electrolysis process to generate a solution with an effective amount of hypochlorite is decreased. The amount of voltage provided by the power source 137 to the electrodes 135 is therefore a balance between the cost of the power source 137 versus the amount of time it takes to generate the hypochlorite. In certain embodiments, when about 9 volts of power is provided by the power source 137 to the electrodes 135 for about 60 seconds to a precursor solution of 3% NaCl, the resulting hypochlorite solution will have up to about 185 ppm hypochlorite, which is an amount that has been found to have significant teeth whitening efficacy. In certain embodiments, even if the power source 137 provides step-wise lower voltages over the course of several electrolysis treatments, due to discharge of the power source 137 during each successive treatment, the resulting hypochlorite solution can still have significant teeth whitening efficacy even though each successive electrolysis treatment may be performed with a lower voltage than previous treatments. Of course, use of a rechargeable battery or an external power source can completely eliminate such a step-wise reduction in power applied to the electrodes 135 during the electrolysis process over time.

The orientation switch 139 is oriented with respect to the open end 117 such that when the container 113 is oriented to hold a liquid, i.e., the open end 117 is oriented upward, the orientation switch 139 is configured to switch to a closed position in which electricity can pass through the orientation switch 139. At other orientations, the orientation switch 139 remains in an open position in which electricity does not pass through the orientation switch 139. In certain embodiments, the orientation switch 139 may be a switch that is actuated by the user to indicate that the open end 117 of the container 113 is oriented upward.

The control circuit 141 is configured to enable the power source 137 to provide operating power to the electrodes 135. In certain embodiments, the control circuit 141 is configured to enable the power source 137 to provide operating power to the electrodes 135 for a predetermined time period. The control circuit 141 starts providing operating power to the electrodes 135 when the control circuit 141 determines that the electrodes 135 pass an electric current above a predetermined current threshold and the container 113 is oriented in the upright position, as determined by the orientation switch 139. In certain embodiments, the control circuit 141 may be a programmable microchip or processor. In certain embodiments the orientation switch 139 may be incorporated as part of the control circuit 141. In such embodiments, the orientation switch 139 may comprise an accelerometer that is formed as part of a programmable microchip or processor that forms the control circuit 141.

In embodiments in which the power source 137 provides approximately 9 volts of power to the electrodes 135 and the control circuit 141 operates the electrodes 135 for a predetermined time period, the predetermined time period may be about 60 seconds. In certain embodiments, the predetermined time period may be a longer or shorter time period when the power source 137 provides approximately 9 volts of power. In other embodiments, the predetermined time period may be determined based on the amount of power available from the power source 137 in relation to the amount of hypochlorite that is desired in solution following the electrolysis process. The predetermined time period, and the inclusion thereof, is not to be limiting of the invention unless otherwise stated in the claims.

The electrolysis circuit 131 may also include an LED 153 which can be used to indicate an ongoing electrolysis process, i.e., when the power source 137 is providing operating power to the electrodes 135 during the predetermined time period. The LED 153 is positioned on an external surface of the housing 111 so that it is visible to the user when the container 113 is oriented in the upright position. In certain embodiments, when the electrolysis process is ongoing, the control circuit 141 is configured to provide power to the LED 153 during the predetermined time period so that an indicator light is emitted. In such embodiments, following completion of the electrolysis process, the control circuit 141 is configured to cease providing power to the LED 153.

Figure 4:
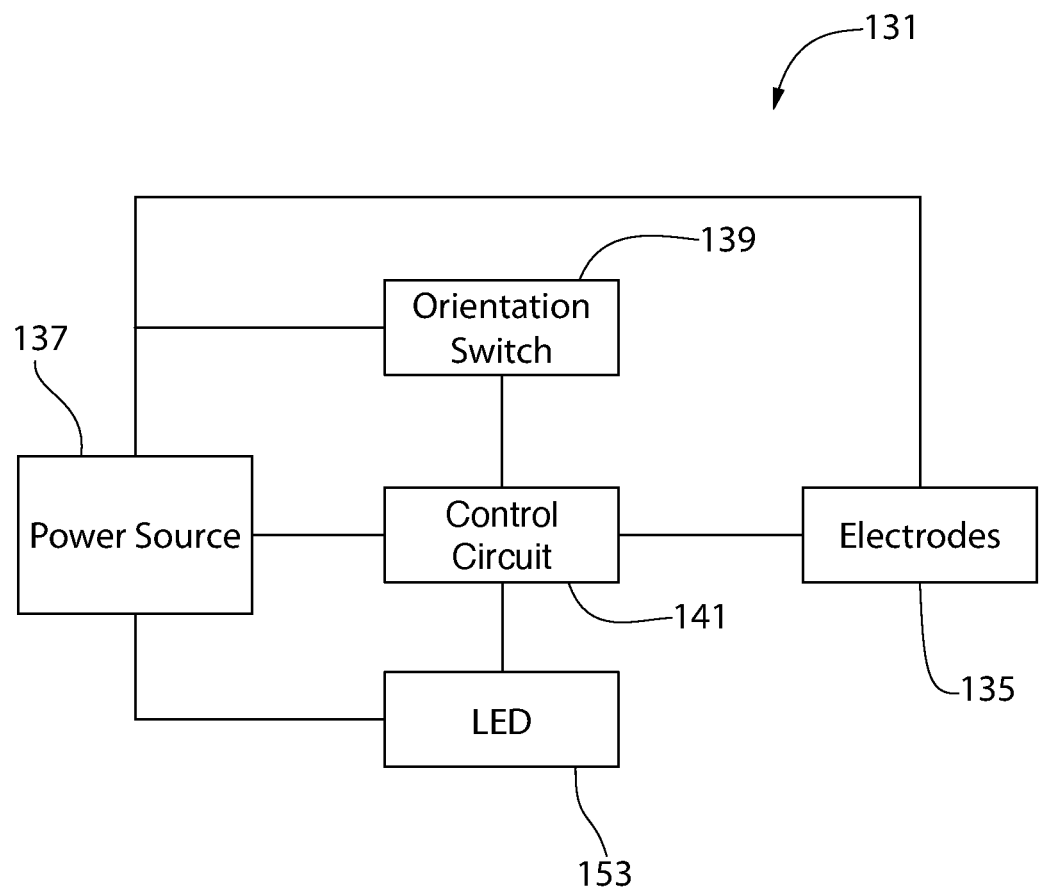
FIG. 4 schematically illustrates the circuit of the electrolysis device of FIG. 1.

An embodiment of the electrolysis circuit 131 is shown in FIG. 4. In this embodiment, the power source 137 is directly electrically coupled to each of the electrodes 135, the orientation switch 139, the control circuit 141, and the LED 153. The electrical circuit between the power source 137, on the one hand, and each of the electrodes 135, the orientation switch 139, and the LED 153, on the other hand, is completed through the control circuit 141. When the orientation switch 139 is in the closed position, the electrical circuit between the power source 137 and the orientation switch 139 is completed through control circuit 141, and the control circuit 141 is configured to sense this completed electrical circuit. Upon completion of the electrical circuit between the orientation switch 139 and the power source 137, the control circuit 141 is configured to determine whether a current, which meets or exceeds a predetermined current threshold, is passing through the electrodes 135. Generally, a current that meets or exceeds the predetermined current threshold will pass through the electrodes 135 when a solution sufficiently fills the space between the two electrodes 149A, 149B. Particularly, the predetermined current threshold is set based upon the current that would pass through the electrodes when an appropriate precursor solution sufficiently fills the space between the two electrodes 149A, 149B. When a both the orientation switch 139 is closed and the current passing through the electrodes 135 meets or exceeds the predetermined current threshold, then the control circuit 141 begins control of the electrolysis process. Following the end of the electrolysis process, which in certain embodiments may be the end of the predetermined time period, the control circuit 141 is configured to open the circuit between the power source 137 and the electrodes 135 and to not close that circuit again until after the orientation switch 139 switches at least once from the closed position to the open position.

Those of skill in the art will recognize that the electrolysis circuit 131 may have different configurations other than shown in FIG. 4 and described in the preceding paragraph while still maintaining similar functionality. The configuration of the electrolysis circuit 131, therefore, is not to be limiting of the invention unless otherwise stated in the claims.

Figure 5:
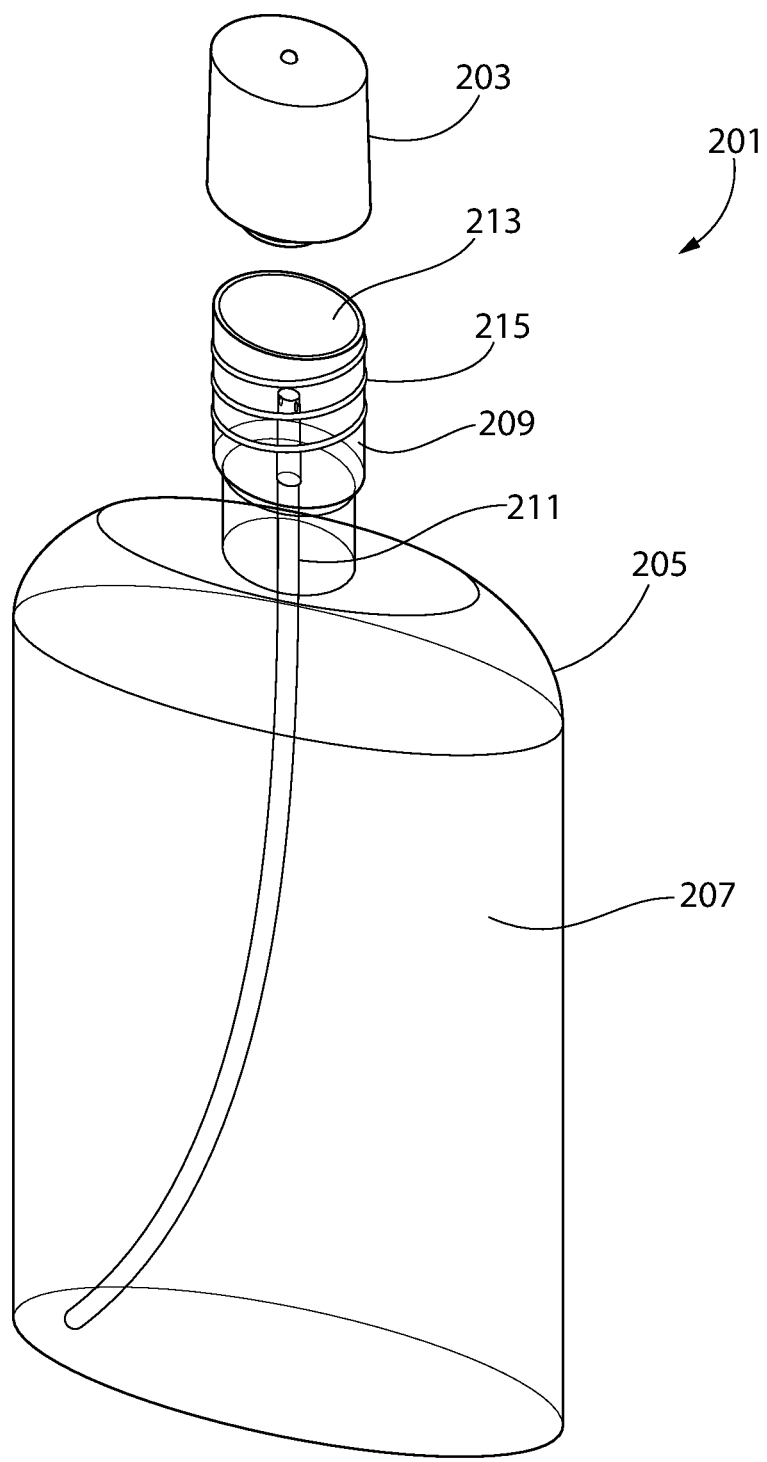
FIG. 5 illustrates a system for delivering a hypochlorite solution in accordance with an embodiment of the present invention.
Figure 6:
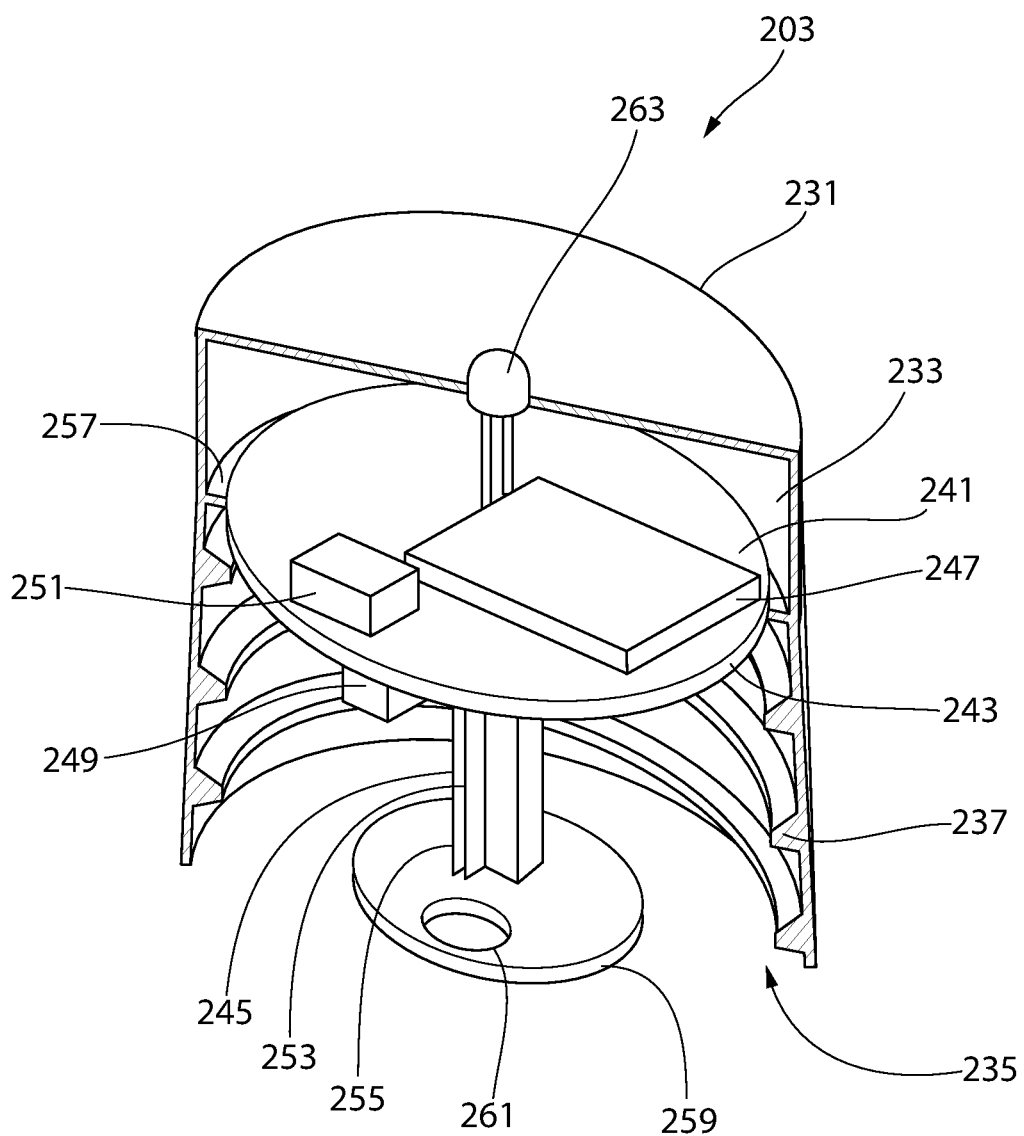
FIG. 6 illustrates a cross sectional view of the cap of the system of FIG. 5.

FIGS. 5-6, illustrate a system 201 for delivering a hypochlorite solution to a user. The system includes an electrolysis device 203 and a bottle 203, each configured to sealingly couple to the other. The bottle 203 includes a first container 207 and a second container 209, with the second container 209 located above and coupled to the first container 207. A tube 211 extends between and fluidically couples the first container 207 to the second container 209. A precursor solution may be stored within the first container 207, and when pressure is applied to the side walls of the first container 209 by a user, the applied pressure pushes the precursor solution through the tube 211 and into the second container 209. The second container 209 includes an open end 213 so that the second container 209 is formed as a cup. The second container 209 also includes threads 215 extending outward therefrom. In certain embodiments, the threads 215 may be omitted.

The electrolysis device 203, as shown in FIG. 6, includes a housing 231 which forms an enclosure 233 and an open-ended cavity 235. The open-ended cavity 235 includes threads 237 extending inward therefrom, and the open-ended cavity 235 and the threads 237 are arranged to threadably engage the threads 215 extending outward from the second container 209 so that the electrolysis device 203 may be affixed to and sealingly engage the second container 209. In certain embodiments, the threads 237 may be omitted.

The enclosure 233 in the embodiment shown is a sealed enclosure in which components of the electrolysis device 203 are located. In certain embodiments, the enclosure 233 may have an access door to provide a user with access to the components of the electrolysis device 203 located within the enclosure 233. In certain other embodiments, the enclosure 233 may have an open access window to provide a user with access to the components of the electrolysis device 203 located within the enclosure 233.

The electrolysis device 203 includes an electrolysis circuit 241 which is configured to control the electrolysis process for the precursor solution within the second container 209. The electrolysis circuit 241 includes a circuit board 243 located within the enclosure 233. The circuit board 243 facilitates electrical coupling of the other components to each other, in that all other components of the electrolysis circuit 241 may be electrically coupled to the circuit board 243. In certain embodiments, the circuit board 243 may be excluded from the electrolysis circuit 241, and in such embodiments the other components of the electrolysis circuit 241 may be directly electrically coupled to each other as needed for proper functioning of the electrolysis circuit 241. In certain other embodiments, some of the components of the electrolysis circuit 241 may be electrically coupled to the circuit board 243, while others are electrically coupled directly to each other. The electrolysis circuit 241 includes a plurality of electrodes 245 located within the open-ended cavity 235. A pressure switch 249 extends into the open-ended cavity 235. Other components of the electrolysis circuit 241 are located within the enclosure 233, including: a power source 247 and a control circuit 251. With the electrodes 245 and the pressure switch 249 located in the open-ended cavity 235 and the circuit board 243 located in the enclosure 233, separated by the wall 257, it is necessary for an electrical connection between these two components. The circuit board 243 should be protected from the precursor solution by a protective silicone barrier or any other appropriate material that provides a barrier against moisture and is non-reactive with the precursor solution. In certain embodiments, it may be desirable for the wall 257 to be entirely covered within the cavity 235 with a silicone barrier to ensure that moisture does not permeate into the enclosure 233 and degrade the components of the electrolysis circuit 241 therein.

The plurality of electrodes 245 includes a first electrode 253 and a second electrode 255 secured between the wall 257 and an end plate 259, with each of the electrodes 245 being electrically coupled to the circuit board 243. The end plate 259 includes a hole 261 through which the tube 211 passes when the electrolysis device 203 is coupled to the second container 209 of the bottle 205. The first and second electrodes 253, 255 are formed as parallel plate electrodes in the embodiment shown, in a manner similar to the electrodes 135 described in connection with and shown in FIG. 3.

The power source 247 provides operating power to each of the other components of the electrolysis circuit 241, and in the embodiment shown, the power source 247 is a battery. In certain embodiments, the power source 247 may be a rechargeable battery. In still other embodiments, the power source 247 may be an external power source. In certain embodiments, the power source 247 provides up to 9 volts of power to the electrodes 245. In still other embodiments, the power source 247 may provide more or less voltage to the electrodes 245. However, when less voltage is provided to the electrodes 245, the time period needed for the electrolysis process to generate a solution with an effective amount of hypochlorite is increased. Similarly, when a greater voltage is provided to the electrodes 245, the time period needed for the electrolysis process to generate a solution with an effective amount of hypochlorite is decreased. The amount of voltage provided by the power source 247 to the electrodes 245 is therefore a balance between the cost of the power source 247 versus the amount of time it takes to generate the hypochlorite.

The pressure switch 249 is positioned within the open-ended cavity 235 such that when the electrolysis device 203 is coupled to the second container 209 of the bottle 205, pressure is applied to the pressure switch 249 by the top wall of the second container 209, and the pressure switch 249 is switched to a closed position in which electricity can pass through the pressure switch 249. In certain embodiments, the pressure switch 249 may be a single pole, single throw type switch that is biased to the open position. In certain embodiments, the pressure switch 249 may be a switch that is actuated by the user to indicate that the electrolysis device 203 is coupled to the second container 209 of the bottle 205.

The control circuit 251 is configured to enable the power source 247 to provide operating power to the electrodes 245. In certain embodiments, the control circuit 251 is configured to enable the power source 247 to provide operating power to the electrodes 245 for a predetermined time period. The control circuit 251 starts providing operating power to the electrodes 245 when the control circuit 251 determines that the electrodes 245 pass an electric current above a predetermined current threshold and the pressure switch 249 is in the closed position. In certain embodiments, the control circuit 251 may be a programmable microchip or processor.

In embodiments in which the power source 247 provides approximately 9 volts of power to the electrodes 245 and the control circuit 251 operates the electrodes 245 for a predetermined time period, the predetermined time period of the control circuit 251 may be about 60 seconds. In certain embodiments, the predetermined time period may be a longer or shorter time period when the power source 247 provides approximately 9 volts of power. In other embodiments, the predetermined time period may be determined by the amount of power available from the power source 247 in relation to the amount of hypochlorite that is desired in solution following the electrolysis process. The predetermined time period, and the inclusion thereof, is not to be limiting of the invention unless otherwise stated in the claims.

The electrolysis circuit 241 may also include an LED 263 which can be used to indicate an ongoing electrolysis process, i.e., when the power source 247 is providing operating power to the electrodes 245. The LED 263 is positioned on an external surface of the housing 231 so that it is visible to the user when the electrolysis device 203 is coupled to the second container 209 of the bottle 205. In certain embodiments, when the electrolysis process is ongoing, the control circuit 251 is configured to provide power to the LED 263 during the predetermined time period so that an indicator light is emitted. In such embodiments, following completion of the electrolysis process, the control circuit 251 is configured to cease providing power to the LED 263.

Figure 7:
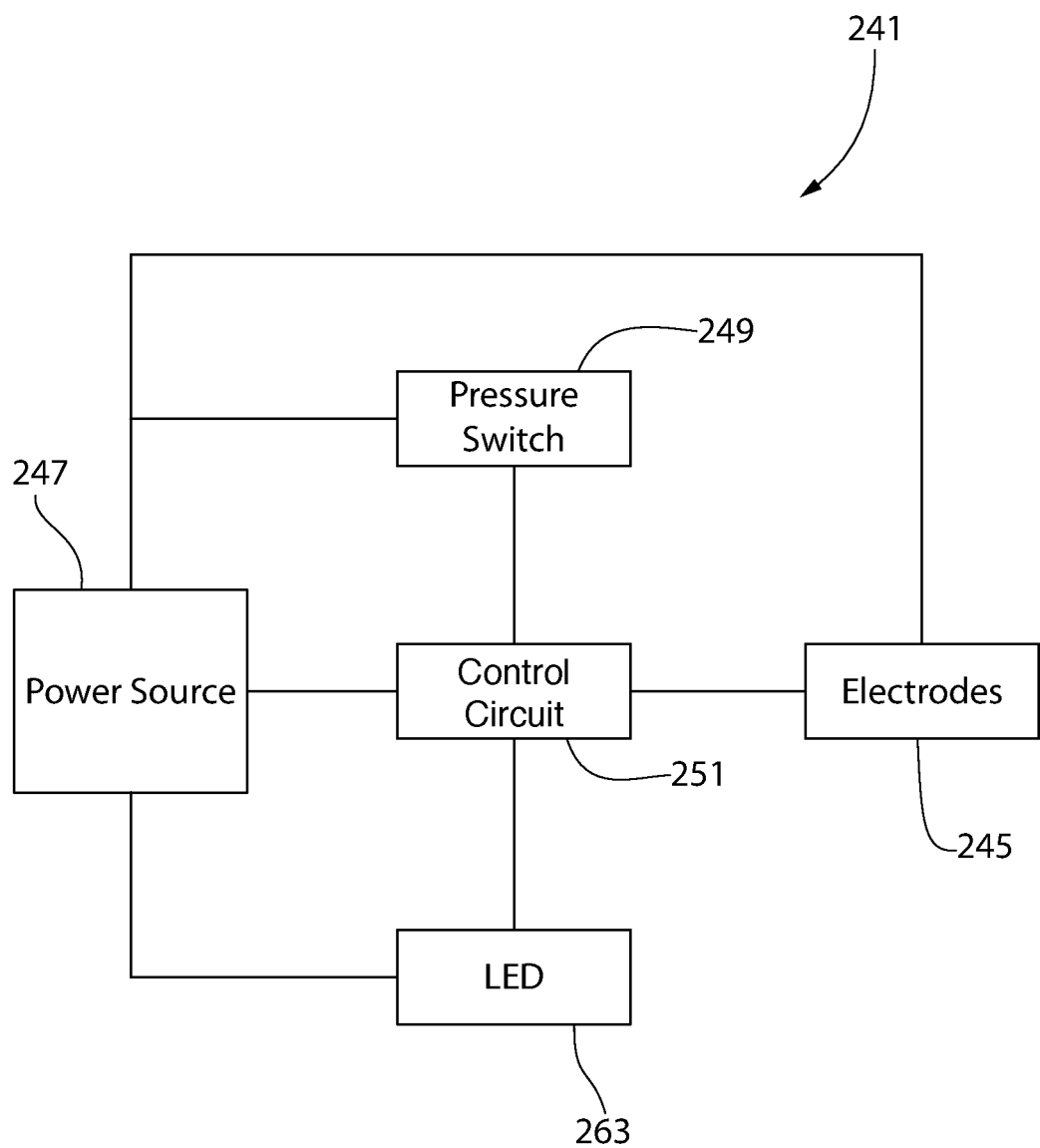
FIG. 7 schematically illustrates the circuit of the electrolysis device of FIG. 6.

An embodiment of the electrolysis circuit 241 is shown in FIG. 7. In this embodiment, the power source 247 is directly electrically coupled to each of the electrodes 245, the pressure switch 249, the control circuit 251, and the LED 263. The electrical circuit between the power source 247, on the one hand, and each of the electrodes 245, the pressure switch 249, and the LED 263, on the other hand, is completed through the control circuit 251. When the pressure switch 249 is in the closed position, the electrical circuit between the power source 247 and the pressure switch 249 is completed through control circuit 251, and the control circuit 251 is configured to sense this completed electrical circuit. Upon completion of the electrical circuit between the pressure switch 249 and the power source 247, the control circuit 251 is configured to determine whether a current, which meets or exceeds a predetermined current threshold, is passing through the electrodes 245. When both the pressure switch 249 is closed and the current passing through the electrodes 245 meets or exceeds the predetermined current threshold, then the control circuit 251 begins control of the electrolysis process. Following the end of the electrolysis process, which in certain embodiments may be the end of the predetermined time period, the control circuit 251 is configured to open the circuit between the power source 247 and the electrodes 245 and to not close that circuit again until after the pressure switch 249 switches at least once from the closed position to the open position.

Those of skill in the art will recognize that the electrolysis circuit 241 may have different configurations other than shown in FIG. 7 and described in the preceding paragraph while still maintaining similar functionality. The configuration of the electrolysis circuit 241, therefore, is not to be limiting of the invention unless otherwise stated in the claims.

EXAMPLE

Figure 8:
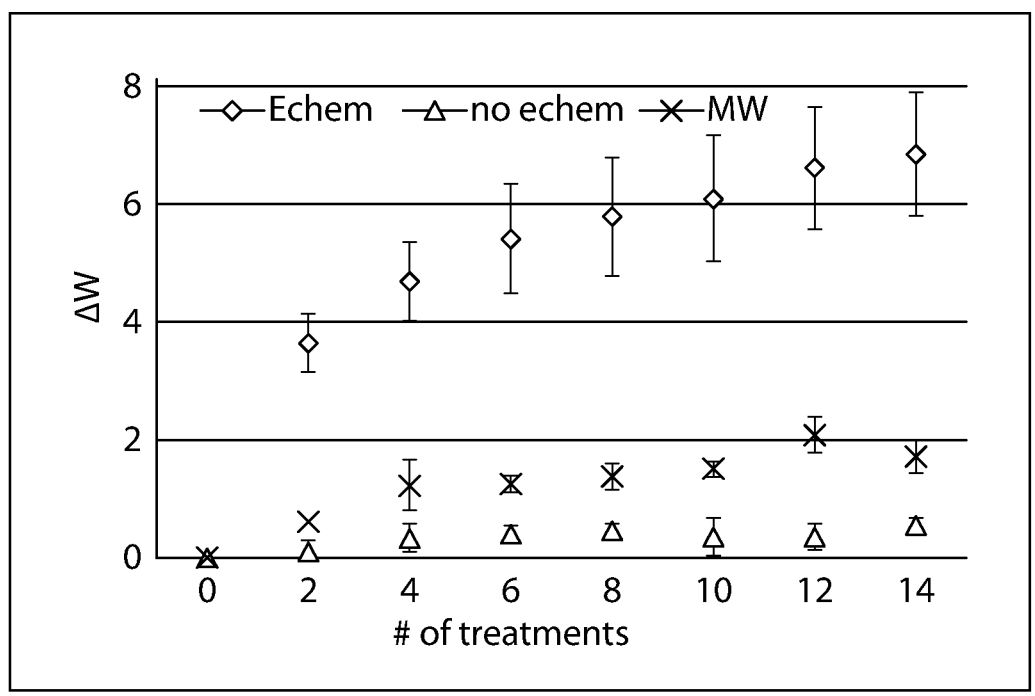
FIG. 8 is a chart showing the expected teeth whitening effects of hypochlorite.

A chart 301 approximating the expected whitening efficacy of a hypochlorite solution for a user is shown in FIG. 8. The data displayed in this chart was generated through the use of artificially stained bovine teeth, each of which underwent several stages of treatment with one of the following: 1) a hypochlorite solution with a pH of about 6.6-6.7 (labeled "Echem"), this solution resulting from an in-situ electrolysis process contemporaneous with data collection; 2) a 3% sodium chloride solution having a pH of about 6.5 (labeled "no echem"), this solution not undergoing any electrolysis process; and 3) a common off-the-shelf mouthwash (labeled "MW") that was marketed as a teeth whitening mouth wash and contained approximately 2% hydrogen peroxide. The bovine teeth were evaluated using the CIELAB color space, as defined by the International Commission on Illumination (CIE), both before and during treatment. Before treatment, the bovine teeth were selected to have an L* value between 58 and 63, and the a* and b* values for each tooth was measured. These initial L*, a*, and b* values were used to calculate the baseline white value, $W^*_{baseline}$, which was used to evaluate the whitening performance of each of the different treatment solutions. All white values W* calculated from the L*a*b* measurements during this evaluation were calculated as:

$$W^* = \sqrt{a^{*2} + b^{*2} + (L^* - 100)^2}.$$

During each stage of treatment, each sample tooth was soaked in a bath of the respective solution for about 60 seconds and then rinsed under running tap water for about 20 second. After each stage of treatment, the L*, a*, and b* values of each sample tooth were again measured, and a treated white value, $W^*_{treated}$, was calculated for each tooth. The change in the white value ΔW* at each treatment stage was calculated as:

$$\Delta W^* = |W^*_{treated} - W^*_{baseline}|.$$

It should be noted that the greater the calculated change in the white value ΔW*, the whiter the subject tooth was as compared to the baseline measurement. As can be seen in the chart 301, over fourteen stages of treatment, the hypochlorite solution generated contemporaneously in-situ had a significantly better whitening efficacy as compared to either of the other two solutions.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An electrolysis device comprising: a housing comprising a container having an open end, the container is filled with a precursor solution when the container is oriented in an upright position; and an electrolysis circuit comprising: a power source; a plurality of electrodes disposed within the container and electrically coupled to the power source; an orientation switch electrically coupled to the power source, coupled to the housing, and oriented to switch to a closed position when the container is oriented in the upright position; and a control circuit electrically coupled to the power source, the electrodes, and the orientation switch, wherein the electrolysis circuit is configured to operate when the electrodes pass an electric current above a predetermined current threshold and the container is oriented in the upright position; wherein the precursor solution comprises NaCl.

2. The electrolysis device of claim 1, wherein the housing comprises an enclosure, and the power source, the orientation switch, and the control circuit are located within the enclosure.

3. The electrolysis device of claim 1, wherein the precursor solution has a pH of between about 6.0-7.0.

4. The electrolysis device of claim 1, wherein the electrolysis circuit is configured to operate for a predetermined time period when the electrodes pass the electric current above the predetermined current threshold and the container is oriented in the upright position.

5. The electrolysis device of claim 4, wherein the predetermined time period is 60 seconds.

6. The electrolysis device of claim 4, further comprising an LED coupled to the housing and positioned to be externally visible, the LED electrically coupled to the control circuit, and the control circuit configured to illuminate the LED during the predetermined time period.

7. The electrolysis device of claim 1, wherein the control circuit electrically couples the electrodes to the power source when the container is oriented in the upright position.

8. A system for delivering an oral care solution, the system comprising:
an electrolysis device comprising:
a housing comprising a first container having an open end, the first container configured to contain a liquid when the first container is oriented in an upright position; and
an electrolysis circuit comprising:
a power source;
a plurality of electrodes disposed within the container and electrically coupled to the power source;
an orientation switch electrically coupled to the power source, coupled to the housing, and oriented to switch to a closed position when the first container is oriented in the upright position; and
a control circuit electrically coupled to the power source, the electrodes, and the orientation switch, wherein the electrolysis circuit is configured to operate when the electrodes pass an electric current above a predetermined current threshold and the first container is oriented in the upright position; and
a second container configured to contain a precursor solution, wherein the housing of the electrolysis device comprises a first threaded coupling, and an opening of the second container comprises a second threaded coupling, the first threaded coupling configured to threadably engage the second threaded coupling such that the housing seals the second container.

9. The electrolysis device of claim 8, wherein the housing comprises an enclosure, and the power source, the orientation switch, and the control circuit are located within the enclosure.

10. The electrolysis device of claim 8, wherein the electrodes are configured to pass the electric current above the predetermined current threshold when the first container is filled with a precursor solution.

11. The electrolysis device of claim 10, wherein the precursor solution comprises NaCl.

12. The electrolysis device of claim 10, wherein the precursor solution comprises a solution of 3% NaCl.

13. The electrolysis device of claim 10, wherein the precursor solution has a pH of between about 6.5-7.

14. The electrolysis device of claim 8, wherein the electrolysis circuit is configured to operate for a predetermined time period when the electrodes pass the electric current above the predetermined current threshold and the container is oriented in the upright position.

15. The electrolysis device of claim 14, wherein the predetermined time period is at least 60 seconds.

16. The electrolysis device of claim 14, further comprising an LED coupled to the housing and positioned to be externally visible, the LED electrically coupled to the control circuit, and the control circuit configured to illuminate the LED during the predetermined time period.

17. The electrolysis device of claim 8, wherein the control circuit electrically couples the electrodes to the power source when the first container is oriented in the upright position.

18. A system for delivering an oral care solution, the system comprising:
a bottle comprising a first container, a second container positioned above the first container, and a tube fluidically coupling the first container to the second container, wherein the second container includes an open end;
a cap comprising an electrolysis circuit and a housing, the housing configured to couple to the second container at the open end, the electrolysis circuit comprising:
a power source;
a plurality of electrodes extending away from the housing and electrically coupled to the power source;
a pressure switch electrically coupled to the power source and positioned to be switched to a closed position when the cap is coupled to the second container; and
a control circuit electrically coupled to the power source, the electrodes, and the pressure switch, wherein the electrolysis circuit is configured to operate when the electrodes pass an electric current above a predetermined current threshold and the pressure switch is in the closed position.

* * * * *